(12) United States Patent
Flores et al.

(10) Patent No.: US 7,820,200 B2
(45) Date of Patent: Oct. 26, 2010

(54) PHARMACEUTICAL COMPOSITION FOR THE SUSTAINED RELEASE OF HYDRALAZINE AND USE THEREOF AS A SUPPORT FOR CANCER TREATMENT

(76) Inventors: Luis Estrada Flores, Calzada de Tlalpan 4369, Col. Torielo Guerra, C.P. 14050 (MX); Alfonso Dueñas González, Calzada de Tlalpan 4369, Col. Torielo Guerra (MX) CP 14050; Arturo Borbolla García, Calzada de Tlalpan 4369, Col. Torielo Guerra (MX) CP 14050; Raul Serna Martinez, Calzada de Tlalpan 4369, Col. Torielo Guerra (MX) CP 14050; Alfredo Rivera Hernández, Calzada de Tlalpan 4369, Col. Torielo Guerra (MX) CP 14050; Alejandro Mohar Betancourt, Calzada de Tlalpan 4369, Col. Torielo Guerra (MX) CP 14050

( * ) Notice: Subject to any disclaimer, the term of this patent is extended or adjusted under 35 U.S.C. 154(b) by 490 days.

(21) Appl. No.: 11/575,016

(22) PCT Filed: Sep. 9, 2004

(86) PCT No.: PCT/MX2004/000064

§ 371 (c)(1),
(2), (4) Date: Oct. 12, 2007

(87) PCT Pub. No.: WO2006/028362

PCT Pub. Date: Mar. 16, 2006

(65) Prior Publication Data

US 2009/0042889 A1    Feb. 12, 2009

(51) Int. Cl.
*A61K 9/22* (2006.01)
(52) U.S. Cl. .................................................. 424/468
(58) Field of Classification Search .................. None
See application file for complete search history.

(56) References Cited

U.S. PATENT DOCUMENTS

| 4,521,402 A * | 6/1985 | Dunn ........................ 424/480 |
| 4,606,909 A | 8/1986 | Bechgaard et al. |
| 4,952,402 A | 8/1990 | Sparks et al. |

* cited by examiner

*Primary Examiner*—Robert A Wax
*Assistant Examiner*—Jeffrey T Palenik
(74) *Attorney, Agent, or Firm*—Reinhart Boerner Van Deuren, P.C.

(57) ABSTRACT

The invention relates to a substained release form of hydralazine for use in cancer therapy. The substained release form of hydralazine can be used to obtain a constant concentration of the active principle in the blood, thereby enabling the demethylating effect of the hydralazine without producing the hypotensive action thereof, such that the inventive composition can be used in cancer therapy.

12 Claims, 4 Drawing Sheets

HYDRALAZINE ER
% RELEASED WITH 35% METHOLOSE 90SH, 35% HYDRALAZINE AND 20% PREGEL STARCH - HIGUCHI

PHARMACEUTICAL COMPOSITION FOR THE SUSTAINED RELEASE OF HYDRALAZINE AND USE THEREOF AS A SUPPORT FOR CANCER TREATMENT

CROSS-REFERENCE TO RELATED PATENT APPLICATIONS

This patent application is the National Stage of International Application No. PCT/MX2004/000064 filed Sep. 9, 2004, the entire disclosure of which is hereby incorporated by reference.

TECHNICAL FIELD OF INVENTION

The present invention relates to the field of pharmaceutical products, more particularly it relates to a pharmaceutical dosage form for the extended release of Hydralazine, which is useful as a reactivator for methylated suppressor genes not expressed during the development of malignant illnesses such as cancer. Therefore said sustained release pharmaceutical form can be used as support in cancer therapy.

BACKGROUND OF THE INVENTION

At experimental level, Hydralazine has shown the demethylating effect on various suppressor genes, which proves that said effect is not specific to a single gene. Both the demethylating effect and the reactivating effect of hydralazine on suppressor genes had been confirmed in vitro and in vivo.

Tablets are solid pharmaceutical dosage forms containing one or more active ingredients generally blended with suitable excipients, and are administered by different routes. Tablets are elaborated by compression of powders or granules, using mechanical equipments fitted with adequate dies and punches. Excipients such as diluents, binding agents, disintegrating agents and lubricants are normally used when formulating tablets. Other ingredients such as colorants and flavoring agents can also be present. Three general methods are used for making tablets: wet granulation, dry granulation, and direct compression.

Tablets may be coated to protect its components against effects from air, humidity or light, to mask unpleasant tastes or odors, to improve appearance, and to control the site of release of the active ingredient in the gastrointestinal tract.

Tablets with simple coating—In some cases tablets are coated with sugar (dragees), which is applied by means of aqueous suspensions. Thereafter, coated tablets are subject to polishing using diluted solutions of wax in solvents such as chloroform or powder blends. Coatings made of substances such as shellac or cellulose acetophtalate are often applied with non-aqueous solvents prior to sugar coating application.

Tablets with enteric coating—When the active ingredient is susceptible of degradation or neutralization by gastric fluids, or where it can irritate gastric mucous lining, the use of an enteric coating is recommended. Such coating is designed to delay the release of the active principle until the tablet has passed through the stomach. The term delayed release is used in the Mexican Pharmacopoeia, Seventh Edition, and relevant monographs include assays and specifications concerning to the release of the active ingredient.

Extended Release Tablets—These are formulated such that the release of the active ingredient occurs for an extended period of time after dose administration. Expressions such as prolonged release; prolonged action; repeated action; and sustained release are also used to describe such pharmaceutical dosage forms. The term extended release, however, is used for pharmacopoeial purposes and release requirements.

Oral Extended Release dosage forms—When a drug is orally administrated in multiple doses using a conventional pharmaceutical dosage form (e.g., tablet, sugar coated tablet, capsule), and the plasma concentration curve of the drug is analyzed over time, a typical graph is observed according to which therapeutically effective levels of drug in plasma are achieved only for a relatively short period of time. Case 1: This is the ideal situation. Plasma drug concentrations are continuously within the therapeutical level (security margin or therapeutical index). Case 2: Curve peaks reach toxic levels (MTC=20 mg/mL); with potential occurrence of drug related adverse reactions (AR) and signs of intoxication. Case 3: Minimal plasma concentration (MPC=10 mg/mL) is within the level of ineffectiveness.

In order to avoid the occurrence of this disadvantages, and at the same time achieve the three basic objectives above mentioned, current trends in pharmaceutical research are directed to find solid oral dosage forms which release the active principle not in an sudden manner as in the conventional solid oral dosage forms, but in a modified and duly controlled mode. Controlled release dosage forms can be grouped, as follows:

Delayed release dosage forms: The active ingredient is released globally, yet not immediately, over a certain period of time (about 2-4 hours) after dosing. The goal is to avoid the action of gastric secretions, such that the drug is contacted with organic fluids only after the oral dosage form has reached the intestinal tract.

These dosage forms correspond to classic oral dosage forms with enteric coating, which are insoluble in the acid gastric media, but soluble in the neutral or slightly alkaline environment and that are prepared by applying to the tablet, sugar coated tablet, or gelatin capsules a thin layer of coating (shellac or varnish) with the solubility characteristics above mentioned.

Extended release dosage forms: Are those dosage forms in which, after an initial release of a certain amount of the active ingredient, said release continues over a period of time (at least 6-8 hours), such that it ensures therapeutically active plasma levels of the drug throughout said period of time. Non-fluctuating therapeutic levels, constantly within de therapeutic range, can be obtained with this type of release system, even without modifications of the dose, or with a relatively longer time interval (for example, 8-12 hours) between doses.

Sustained release dosage forms: In these systems there is an initial, partial release of the active principle the release of which continues in a uniform and constant manner which ensures therapeutically active plasma levels of the drug over a relatively long period of time (12-24 hours). With this type of oral medicine, continuous therapeutic plasma levels can be obtained, always within the safety margin, for periods of time long enough as to enable a very simplified dosage regime of one dose per day, such as the OROS or PUSH-PULL systems.

As is evident in an oral form of administration, the maximum time of sustained release of the medicine is dictated by the time said dosage form takes to transit along the patient's intestinal tract (24-48 hours). Often it is difficult to differentiate between extended release oral forms and sustained release oral forms. For this reason, both systems are now identified as continued release forms, and the term "sustained release" is used for other pharmaceutical forms (specially injectable depots or subcutaneous implants), which allow, with a single dose of medicine, a sustained therapeutical action over very long periods of time (months or even years).

However, since there are considerable variations between extended release oral forms and sustained release oral forms regarding the mechanisms applied to achieve the delaying effect (that is, the mechanism by which the active ingredient is released slowly and gradually), it has been preferred to maintain such distinction, although the difference of results obtained with both forms of release (extended and sustained) sometimes is more theoretical than real.

Regarding hydralazine extended release dosage forms; U.S. Pat. No. 4,606,909 discloses pharmaceutical formulations based on homogeneous pellets that are ultimately coated with a polymer that controls the rate of release. However, what is shown in the specification of this document it can be appreciated that it refers to a chemical form of delayed release, since only the occurrence of the maximum concentration peak is delayed. In this regard, it should be taken in account that the totality of the drug is released only when complete erosion of the coating occurs in the small intestine, at about pH 6.5. Formulations developed by the methods of U.S. Pat. No. 4,606,909 are only suitable to be filled into capsules, since is critical for the pellets to be free and independent from each other. This type of formulation tends to be useful as a method of delayed release system, but not as a method of controlled release.

There are other methods of preparing and designing extended release formulations, such as those described in U.S. Pat. No. 4,952,402 in which a type of microparticles or "pharmasomes" with an extremely small size is provided.

Although in the previous art there are several methods of preparing extended release formulations, each of these formulations is suitable for different and specific types of medicine. None of the methods known from the previous art allows its application to obtain a really useful and effective hydralazine pharmaceutical composition that could be administered in different types of illnesses, among which cancer can be mentioned.

Therefore, one object of this invention is to provide a pharmaceutical formulation in the form of tablets comprising a matrix of polymer, active ingredient and excipients.

Another object of this invention is to provide a drug extended release system that releases the active ingredient at the required rate to reach and maintain a constant concentration of said active principle in blood.

Yet another object of the present invention is to provide an extended release system for a drug such as hydralazine; the release of which being equivalent to an analogous concentration of a continuous intravenous infusion wherein hydralazine is administered to the patient at a constant rate and which is equal to the elimination rate.

Another additional object of the present invention is to provide an hidralazine extended release system, the release rate of which being independent of the amount of hydralazine remaining within the dosage form, said release rate also being constant over a given period of time.

A further object of the present invention is to provide an extended release system based on a hydralazine pharmaceutical composition such that it quickly reaches a therapeutic level and at a sustained and uniform concentration for a given period of time, the form of dosing generally comprises two steps: an initial dose that releases the drug immediately, and a maintenance dose responsible for the extended release suitable for cancer treatment.

DETAILED DISCLOSURE OF THE INVENTION

Figure 1:
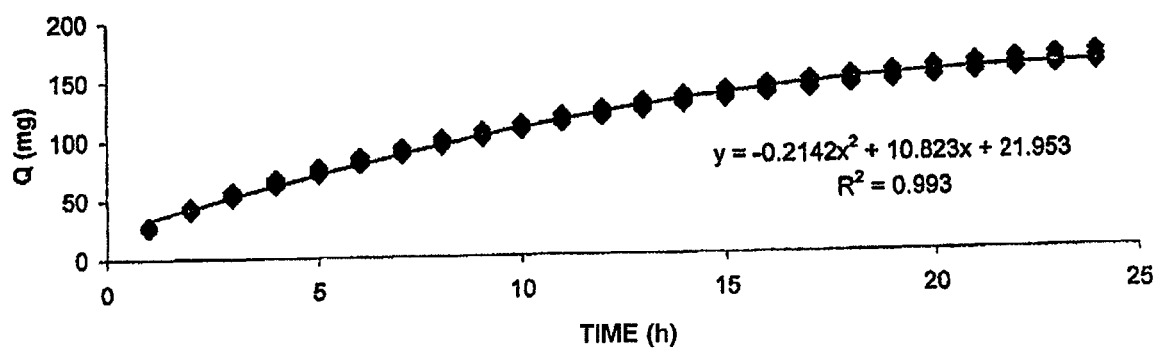
FIG. 1 shows the typical release profile (amount of drug released [Q] versus time), obtained from one of the compositions encompassed by this invention.

The present invention refers to a hydralazine extended release pharmaceutical composition. According to the instant invention, what is pretended is to obtain a pharmaceutical composition such that a therapeutical level could be reached quickly and at a sustained and uniform concentration for a given period of time; the form of dosing generally consists in two steps: an initial dose which immediately releases hydralazine, and a maintenance dose responsible for the sustained release of hydralazine in such ratios that allow that said pharmaceutical composition could be useful for cancer treatment.

Considering the above, the present invention is based on the well-established pharmacokinetic parameters of hydralazine reported in literature. Based on the findings of Dueñas and collaborators (*Reactivation of tumor suppressor genes by the cardiovascular drugs hydralazine and procainamide and their potential use in cancer therapy; in Clinical Research* Vol. 9, 1596-1603, May 2003), what is suitably required are release rates of approximately 7.58 mg/hr during 24 hours, which will make it usable in the reported treatments maintaining the desired demethylating effect and avoiding the hypotensive effect.

The pharmaceutical composition which is the subject matter of this invention is composed as follows: from 10% to 70% hydralazine hydrochloride as the active ingredient; from 3% to 50% of a release rate-limiting polymer selected from some of the following compounds or from a mixture thereof: ethylcellulose, hydroxypropylcellulose, hydroxypropyl methylcellulose, hydroxyethylcellulose, derivatives of methacrylic acid o carbomer, among others; from 15% to 40% of a diluent agent selected from starch, lactose, microcrystalline cellulose, monobasic calcium phosphate or dicalcium phosphate, alcohols derived from carbohydrates such as sorbitol or mannitol or mixtures of all the above; from 5 to 20% of a release rate-moderating hydrophilic polymer selected from starch and its derivatives, alkyl derivatives of cellulose such as methylcellulose, carboxymethylcellulose, carbomer, natural gums such as acacia or xanthan, polyvinylpyrrolidone, carrageenin or mixtures of some or all of the above; from 0.1 to 2% of a lubricant agent such as a metallic stearate, for example magnesium stearate, long chain fatty acids like stearic, palmitic and oleic among others, or a mixture of some of the above, and when desired, a solvent for granulation based on water, short chain organic alcohols, glycols and triols among others.

According to what is shown in the graphics of the Figures accompanying the present invention, the results from different extended release pharmaceutical prepared in accordance with the description of the invention are provided, which consider some of the nearest approximations to the ideal dissolution profile of hydralazine as the active principle.

Example 1

According to the present invention, a hydralazine extended release composition was prepared using the following amounts:

| | |
|---|---|
| HYDROXYPROPYLMETHYLCELLULOSE 2208 USP | 42 to 44% |
| MICROCRYSTALINE CELLULOSE PH 200 | 25 to 28% |
| HYDRALAZINE | 16 to 20% |
| PREGELATINIZED STARCH | 10.00% |
| Mg STEARATE | 0.1 to 2% |

The results of the behavior of this composition are shown in the plot of FIG. 1, which shows the typical release profile (amount of drug released [Q] over time) obtained for one of the exemplary compositions, according to the present invention, and that exhibits a constant release rate for the drug of 10.823 mg/h over a period of approximately 20-22 hours, and then a decrease of said release rate up to the 24th hour.

Figure 2:
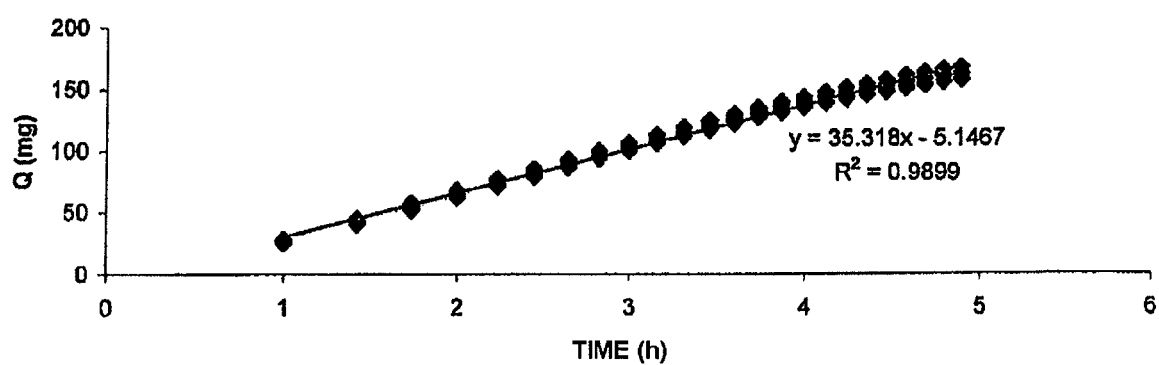
FIG. 2 shows a mathematical transformation of said typical release profile shown in FIG. 1.

This can be appreciated in the plot of FIG. 2, which shows a mathematical transformation of the typical release profile of the composition, prepared in accordance with the present invention, referred to in FIG. 1, according to the Theory of Release by Matrices of T. Higuchi, as described in *Mechanism of Sustained-action Medication. Theoretical Analysis of Rate of Release of Solid Drugs Dispersed in Solid Matrices. Higuchi T. J Pharm Sci.* 1963 December; 52:1145-9), which predicts a linear relationship between the released amount of drug, Q, and the square root of time, $t^{1/2}$, noticing that for this specific case such linear relationship is conserved until about 22 hours.

Example 2

According to the present invention, a hydralazine extended release composition was prepared using the following amounts:

| | |
|---|---|
| HYDROXYPROPYLMETHYLCELLULOSE 2208 USP | 44 to 46% |
| MICROCRYSTALINE CELLULOSE PH 200 | 27 to 29% |
| HYDRALAZINE | 16 to 20% |
| PREGELATINIZED STARCH | 10.00% |
| Mg STEARATE | 0.1 to 2% |

Figure 3:
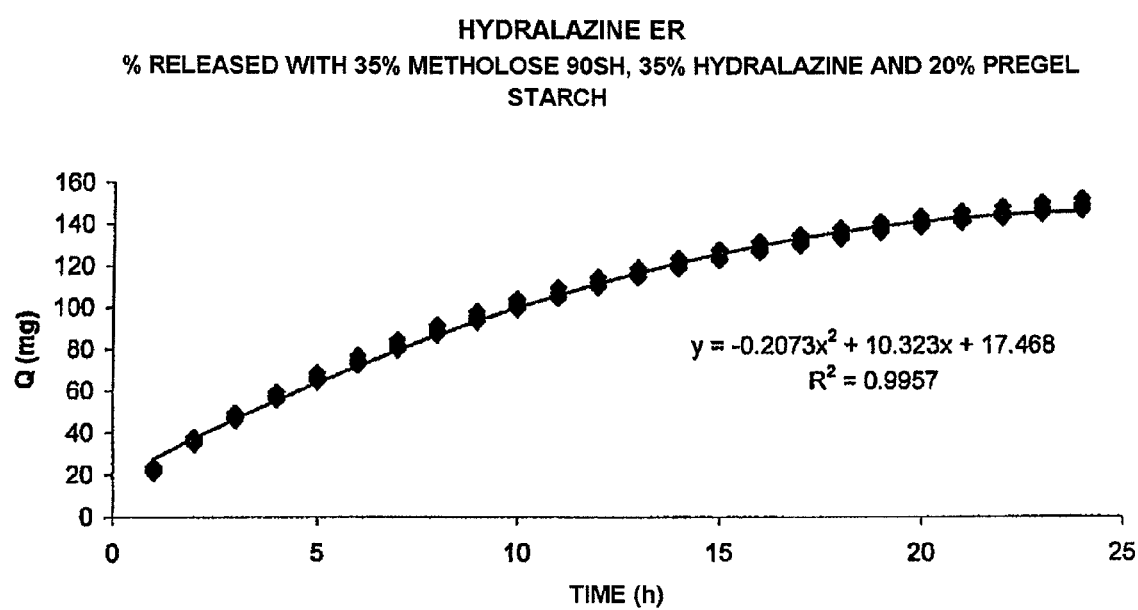
FIG. 3 shows another typical release profile (amount of drug released [Q] versus time), obtained from one of the compositions according to the present invention.

The results of the behavior of this composition are shown in the plot of FIG. 3, in which the other typical release profile (amount of drug released [Q] over time) is shown, obtained for another of the exemplary compositions according to the present invention, and that exhibit a constant release rate for the drug of 10.323 mg/h over a period of approximately 20-22 hours, and then a decrease of said release rate up to the 24th hour.

Figure 4:
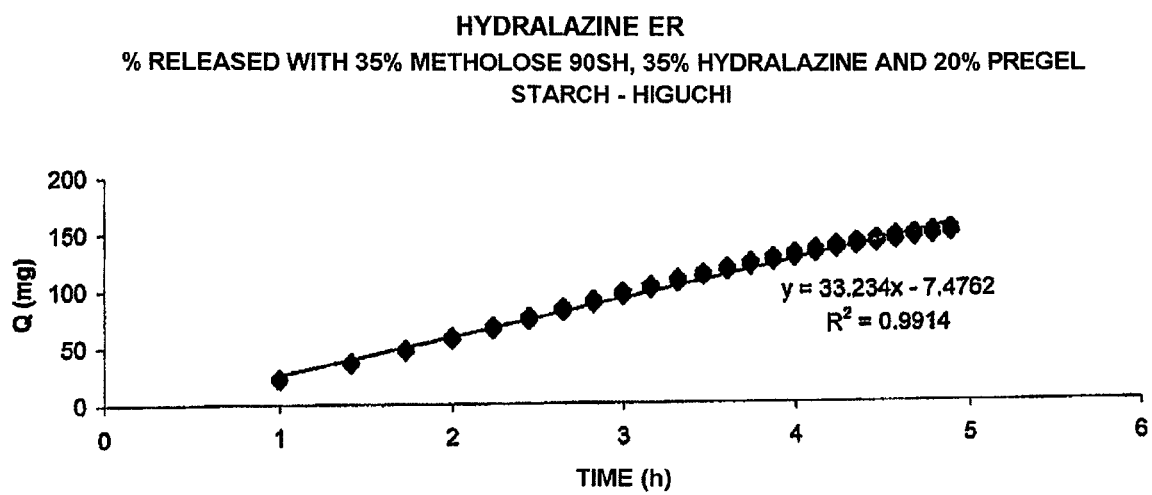
FIG. 4 shows a mathematical transformation of the typical release profile shown in FIG. 3.

Furthermore, the plot of FIG. 4 also shows a mathematical transformation of the typical release profile of the composition prepared in accordance with the present invention, referred to in FIG. 3, according to the Theory of Release by Matrices of T. Higuchi, which predicts a linear relationship between the released amount of drug, Q, and the square root of time, $t^{1/2}$, noticing that for this specific case such linear relationship is conserved until about 22 hours.

The ideal release constant shown is, as it been mentioned, near to 7.5 mg/h, with the release rates shown in the above examples of pharmaceutical compositions of this invention, being release constants of 10 mg/h.

Oral Bio-Availability and Pharmacodynamic Effect Assays

In order to determine the bio-availability characteristics of the composition which is the subject matter of this invention, a clinical study was performed with healthy volunteers to determine oral bioavailability and the pharmacodynamic effect of a single dose of the hydralazine composition in the form of extended release tablets prepared in accordance with the composition set forth in this invention, the objectives of this study are to determine the bio-availability of the hydralazine extended release composition of the present invention in healthy volunteers in a single dose schedule; to characterize the hemodynamic changes induced by the hydralazine extended release composition of this invention, administered in a single dose to healthy volunteers; to compare the pharmacokinetic behavior of the hydralazine extended release composition of the present invention in healthy volunteers, and to establish the differences between populations having a phenotype of slow or fast acetylator. To achieve the above objectives, a hydralazine extended release composition according to the present invention was prepared, in the form of a 182 mg tablet.

What is claimed is:

1. A hydralazine extended release pharmaceutical composition comprising: from 16 to 20% hydralazine hydrochloride as active ingredient; from 42 to 46% of a hydrophilic polymer that limits the release rate of said active ingredient; from 25 to 29% of a diluent agent; 10% of a release rate-moderating hydrophilic polymer; and from 0.1 to 2% of a lubricant agent, wherein neither the release rate-limiting polymer or the release rate-moderating polymer is hydrophobic in any range of pH.

2. A hydralazine extended release pharmaceutical composition according to claim 1, wherein the release rate-limiting polymer is hydroxypropylmethylcellulose.

3. A hydralazine extended release pharmaceutical composition according to claim 1, wherein said diluent agent is microcrystalline cellulose.

4. A hydralazine extended release pharmaceutical composition according to claim 1, wherein the release rate-moderating hydrophilic polymer comprises pregelatinized starch.

5. A hydralazine extended release pharmaceutical composition according to claim 1, wherein said lubricant agent is magnesium stereate.

6. A hydralazine extended release pharmaceutical composition according to claim 1, wherein said composition incorporates a solvent for granulation, wherein the solvent consists of a mix of water and ethanol in a proportion in volume of 1:1.

7. A hydralazine extended release pharmaceutical composition according to claim 1, wherein said composition is used for cancer treatment at release rates of up to 7.58 mg/hr for 24 hours.

8. A hydralazine extended release pharmaceutical composition according to claim 2, wherein said composition is used for cancer treatment at release rates of up to 7.58 mg/hr for 24 hours.

9. A hydralazine extended release pharmaceutical composition according to claim 3, wherein said composition is used for cancer treatment at release rates of up to 7.58 mg/hr for 24 hours.

10. A hydralazine extended release pharmaceutical composition according to claim 4, wherein said composition is used for cancer treatment at release rates of up to 7.58 mg/hr for 24 hours.

11. A hydralazine extended release pharmaceutical composition according to claim 5, wherein said composition is used for cancer treatment at release rates of up to 7.58 mg/hr for 24 hours.

12. A hydralazine extended release pharmaceutical composition according to claim 6, wherein said composition is used for cancer treatment at release rates of up to 7.58 mg/hr for 24 hours.

* * * * *